United States Patent [19]

Pike

[11] Patent Number: 6,033,225
[45] Date of Patent: *Mar. 7, 2000

[54] DEVICE AND METHOD FOR SIMULATING HAZARDOUS MATERIAL DETECTION

[76] Inventor: Steven D. Pike, Argon Electronics, Unit 16 Ribocon Way, Progress Business Park, Luton, Bedfordshire, LU4 9UR, United Kingdom

[*] Notice: This patent is subject to a terminal disclaimer.

[21] Appl. No.: 09/033,904

[22] Filed: Mar. 3, 1998

Related U.S. Application Data

[62] Division of application No. 08/710,530, Sep. 19, 1996, Pat. No. 5,722,835.

[30] Foreign Application Priority Data

Sep. 19, 1995 [GB] United Kingdom .................... 9519098

[51] Int. Cl.⁷ ........................................................ G09B 9/00
[52] U.S. Cl. .............................................. 434/218; 434/219
[58] Field of Search ...................................... 434/218, 219

[56] References Cited

U.S. PATENT DOCUMENTS

| | | | |
|---|---|---|---|
| 3,276,143 | 10/1966 | Jacquiss | 434/218 |
| 3,293,777 | 12/1966 | Shaw | 434/218 |
| 3,636,641 | 1/1972 | Daskam | 434/218 |
| 3,643,166 | 2/1972 | McCurnin | 434/218 |
| 4,500,295 | 2/1985 | Insinger | 434/218 |
| 4,582,491 | 4/1986 | Monteith | 434/218 |
| 4,630,044 | 12/1986 | Polzer | 340/825.72 |
| 4,917,611 | 4/1990 | Whalen | 434/218 |
| 5,304,065 | 4/1994 | Hurst | 434/218 |
| 5,413,482 | 5/1995 | Ward | 434/218 |
| 5,730,602 | 3/1998 | Gierhart | 434/155 |

OTHER PUBLICATIONS

Jane's NBC Protective Equipment, 1995 Edition, Chemical Agent Monitor Simulator, Argon Electronics, Dec. 1995.

*Primary Examiner*—Robert A. Hafer
*Assistant Examiner*—Kurt Fernstrom
*Attorney, Agent, or Firm*—Richard C. Litman

[57] ABSTRACT

The present invention is a device that simulates a radioactive, bacteriological and/or hazardous chemical source and a radioactivity, bacteriological and/or hazardous chemical detector, to train individuals in the correct use of a real radioactivity, bacteriological and/or hazardous chemical detector. A magnet, ultrasound emitter, or passive radio identification device (PRID) is used to simulate the hazardous material source. The PRID may include a magnet. The simulated detector includes a Hall effect device to detect the magnet when used. When the magnet is detected as a trainee moves the simulated detector close to the PRID, the simulated detector outputs a 50 ms RF burst to activate the PRID. The simulated detector may transmit the burst every 250 ms when the magnet is not used in the PRID. Once activated, the PRID waits for completion of the 50 ms pulse, and then transmits a signal that identifies the type of contamination to the simulated detector. The ultrasound emitters and magnet can be used without the need for the RF pulse to simulate a single contamination material, or the ultrasound emitters can use multiple frequencies for different materials. The ultrasound emitters may emit a modulated signal that identifies the type of contamination to the simulated detector, similar to the PRID.

5 Claims, 4 Drawing Sheets

DEVICE AND METHOD FOR SIMULATING HAZARDOUS MATERIAL DETECTION

CROSS REFERENCE TO RELATED APPLICATION

This application is a division of application Ser. No. 08/710,530 filed sep. 19, 1996, now U.S. Pat. No. 5,722,835.

BACKGROUND OF THE INVENTION

1. Field of the Invention

The present invention relates to a device and method for training individuals in the proper use of a detector for sensing specific materials, in particular hazardous materials including radioactive, biological or chemical weapon agents, or hazardous environments, for example in areas where oxygen levels are depleted. The device simulates these hazardous materials and the detector to provide this training without exposure to actual hazardous materials.

2. Description of the Prior Art

Several prior art devices are known for simulating the detection of hazardous materials. The prior art devices, however, fail to disclose the ability to differentiate between different types and/or levels of contamination. In addition, the ability to allow direct instantaneous input by an instructor is also lacking. U.S. Pat. No. 3,276,143, (Jaquiss) discloses a simulated radiac trainer that simulates a radiation source using an RF transmitter and simulates a radiacmeter using an RF receiver. U.S. Pat. No. 3,293,777, (Shaw et al.) discloses a device that uses RF transmitters and a receiver to train individuals in the use of radiation detecting equipment. U.S. Pat. No. 4,500,295, (Insinger, III et al.) discloses a simulated radiation source and detector using a magnet as the simulated radiation source. U.S. Pat. No. 4,582,491, (Monteith) discloses a training apparatus that simulates nuclear, bacteriological and/or chemical contamination by storing locations of simulated contamination and providing appropriate responses based on the location of the apparatus relative to the stored locations. U.S. Pat. No. 5,304,065, (Hurst et al.) discloses a device that operates in a similar fashion to the Monteith apparatus.

Unlike the above prior art devices, the present invention uses an RF identification device for simulating different levels and types of hazardous materials. RF identification devices are known to be used in different environments. U.S. Pat. No. 4,630,044, (Polzer) discloses an information exchange system that uses RF identification devices that include inductively coupled transponders that derive power for transmitting by rectifying a received RF signal. U.S. Pat. No. 5,457,447, (Ghaem et al.) discloses an RF identification device that is powered by various forms of incident energy. U.S. Pat. No. 5,497,140, (Tuttle) discloses an RF identification device in the form of a postage stamp or shipping label. The devices used in U.S. Pat. Nos. 4,630,044, 5,457, 447 and 5,497,140 use similar technology as the passive radio identification devices used in the present invention, and these patents are hereby incorporated by reference.

None of the above inventions and patents, taken either singly or in combination, is seen to describe the instant invention as claimed.

SUMMARY OF THE INVENTION

The present invention is system that includes a device that simulates a specific material or materials, specifically radioactive, bacteriological, and/or hazardous chemical source and a device for detecting these materials, to train individuals in the correct use of an actual device for detecting these materials, specifically radioactive, bacteriological and/or hazardous chemical detectors, without the need to expose these individuals to hazardous materials. In the present document the term "hazardous materials" also includes hazardous environments, for example environments where oxygen levels are depleted. In addition to the increased safety for the individuals involved in the training exercise, the present invention reduces the impact on the environment as no chemical, bacteriological, or radioactive substances are used. While some present methods for simulating hazardous material detection include using materials that are not hazardous to the individuals involved in the training, some of these materials are environmentally unfriendly, and further, water and detergent are needed to wash the simulating materials off of "contaminated" objects. The present invention eliminates all of these environmental hazards, as only water is needed to simulate decontamination. The system includes a device to simulate the hazardous material source, a receiver and microcomputer which simulates the hazardous material detector, and an optional remote control device for active instructor input. The device that simulates the hazardous material source is either: a passive radio identification device, (PRID), (with or without a magnet); a magnet alone; or an ultrasound emitter. The receiver within the simulated hazardous material detector is configured to receive the signal from whatever type of device is used to simulate the hazardous material source, and further the simulated hazardous material detector may contain all three types of receivers, (RF for PRIDs, Hall effect device for magnets, and an ultrasound receiver for ultrasound emitters).

The PRID includes a tuned circuit, an energy storage capacitor, a transmitter unit, a microcomputer and optionally, a permanent magnet. In embodiments where the PRID includes a magnet, the simulated detector includes a Hall effect device to detect the magnet. When the magnet is detected, (when a trainee moves the simulated detector close to the PRID), the simulated detector outputs a 50 ms RF burst. While 50 ms is the preferred length of the RF pulse, the length of the pulse can be adjusted depending on the required energy for the PRID, size of the following energy storage capacitor, etc. The RF pulse resonates the tuned circuit contained within the PRID, and a voltage is developed across the tuned circuit. This voltage charges the energy storage capacitor through a diode. When the capacitor is charged, the microcomputer is activated by the power supplied by the storage capacitor. Once activated, the microcomputer waits for completion of the 50 ms pulse, and then activates the transmitter. The transmitter then transmits a signal that identifies the type and level of contamination, as well as an indication of the PRID's transmitted RF level as a reference to the simulated detector. When the PRID uses a permanent magnet to simulate the contamination, the signal contains an indication of magnetic field strength as a reference. The transmitter uses the tuned circuit as an antenna, and the information is coded in the signal using known frequency shift keying techniques.

The simulated detector includes an RF transmitter and receiver, a microcomputer and a display device. When the simulated detector is to be used with PRIDs having permanent magnets, it is additionally equipped with a Hall effect device, an amplifier and an analog to digital (A/D) converter, to provide the microcomputer with an indication of detected magnetic field strength. If the system includes the instructor's remote, (for active instructor intervention), the simulated detector also includes a suitable receiver, (RF or infrared), to receive and decode the instructor's commands. The simulated detector periodically transmits a 50 ms RF pulse, and then switches to receive mode, to detect any responding PRIDs that may be within range. As described above, a PRID within range will respond to the RF pulse by transmitting a frequency shift keyed identification signal that provides the simulated detector with information about the type and level of contamination, as well as an RF reference concerning the PRID's transmitted RF level. The microcomputer then decodes the PRID's signal, and compares the received RF signal strength to the RF reference to determine the distance the detector is from the PRID. Based on the distance, the level and type of contamination, and the position of simulated controls on the detector, the microcomputer determines an appropriate response. The response is then displayed as an analog meter readout, or digitally using a liquid crystal display, or no response may be indicated if appropriate, (detector set for wrong material detection, detector not close enough, etc.).

The instructor's remote control device contains a keypad and a transmitter, and has a similar configuration to remote controls used for televisions, stereo equipment, etc. The transmitter is infrared or RF depending on the remote control receiver used in the detector simulator. The remote control allows active instructor input. This feature is useful in training exercises, in that it allows the instructor to change certain parameters of the training program. In the course of a training exercise wherein simulated chemical or radioactive contamination is found, the students are often trained in proper decontamination procedures. The students perform these procedures within view of the instructor. If the proper technique is used, the instructor can use the remote to program the simulated detector's microcomputer, to ignore the particular PRID placed on the person or object that has been properly decontaminated. Further, if the decontamination procedure is done partially or completely incorrectly, the instructor can program the microcomputer to give a partial reading, or simply allow the microcomputer to continue to give a full reading. These changes in the simulator detector's responses, can be done without any knowledge on the part of the students, thus the training procedure can follow actual hazardous material detection procedures as closely as possible. For more complex hazardous material detection exercises, the instructor's remote may include a hand held personal computer (PC) with preprogrammed exercise routines stored therein.

While the above embodiments use either a magnet alone, a PRID with a magnet, or a PRID alone, to simulate the specific material being detected, a further embodiment uses ultrasound emitters to simulate the specific material. This is done in one of two ways. The ultrasound emitters transmit an ultrasound signal at a specified frequency, and the simulated detector uses an ultrasound receiver to detect this signal. In one embodiment, this signal is a simple nonmodulated frequency, that is used to simulate a specific material. When more than one material is to be simulated, the ultrasound emitters use more than one frequency. For example, a 25 kHz ultrasound signal may be used to simulate the presence of mustard agent, while a 33 kHz signal is used to simulate the presence of nerve agent. An advantage over the use of PRIDs, in this embodiment, is that the ultrasound emitters can be placed as close to each other as desired without any mutual interference. This allows any size area to be simulated as being contaminated, simply by placing a number of the emitters in a desired pattern. The different frequencies can also be overlapped to simulate two different contaminates occupying the same space. This is possible because the simulated detector has separate receivers for the two frequencies, thus allowing simultaneous processing. In a further embodiment, the ultrasound emitters can be used in place of the PRIDs. This is done by modulating the ultrasound signal, to thereby include the identification signal information encoded therein. The ultrasound receiver in the simulated detector includes a demodulator and an A/D converter to supply the information to the microcomputer inside the simulated detector. When the ultrasound emitters are used to transmit the identification signal, as with the RF PRIDs care must be taken to space the emitters far enough apart to avoid mutual interference.

Some actual hazardous material detectors respond to interfering substances which can lead to confusion on the part of the user of these detectors. This is particularly true with respect to chemical agent detectors used in the presence of fuel vapor. The above described modulated ultrasound emitters are very useful for training individuals in the differentiation between real hazardous materials and interfering substances. The simulated detector in this scenario would respond to simulated interfering signals, (assuming the detector is correctly configured), but not to simulated chemical agent, until the instructor sent an appropriate command using the remote. The use of ultrasound is particularly well suited to the simulation of vapors and gases, as the ultrasound signal can be contained in the same manner as these substances. The use of identified ultrasound signals permits the simulation of explosive and toxic gas for an indication of depletion of oxygen, for example. By using the instructor's remote, (when deemed appropriate), the instructor can arrange for detection of the signal to simulate either a gradual or rapid leak, or can reduce the simulated detector's sensitivity to reduce the reading to simulate venting of the hazardous gas.

Regardless of the type of hazardous material simulator used, the simulated detector can also be programmed to give readings indicative of a failure of the simulated detector or the simulated detector's sensor, (probe). This allows training of individuals in the proper procedure to follow in the event of an actual hazardous material detector failure.

Accordingly, it is a principal object of the invention to provide a method and means of accurately simulating the detection of hazardous materials in a training environment, without the need for exposure to hazardous materials.

It is another object of the invention to provide a device that can simulate the detection of a number of hazardous materials while differentiating between the materials.

It is a further object of the invention to allow an instructor to control the training parameters without any indication to the students that he has done so.

It is still another object of the invention to provide a means of determining whether the correct use of hazardous material detecting equipment has been followed.

It is an object of the invention to provide improved elements and arrangements thereof in a hazardous material detector simulator for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENT(S)

Figure 1:
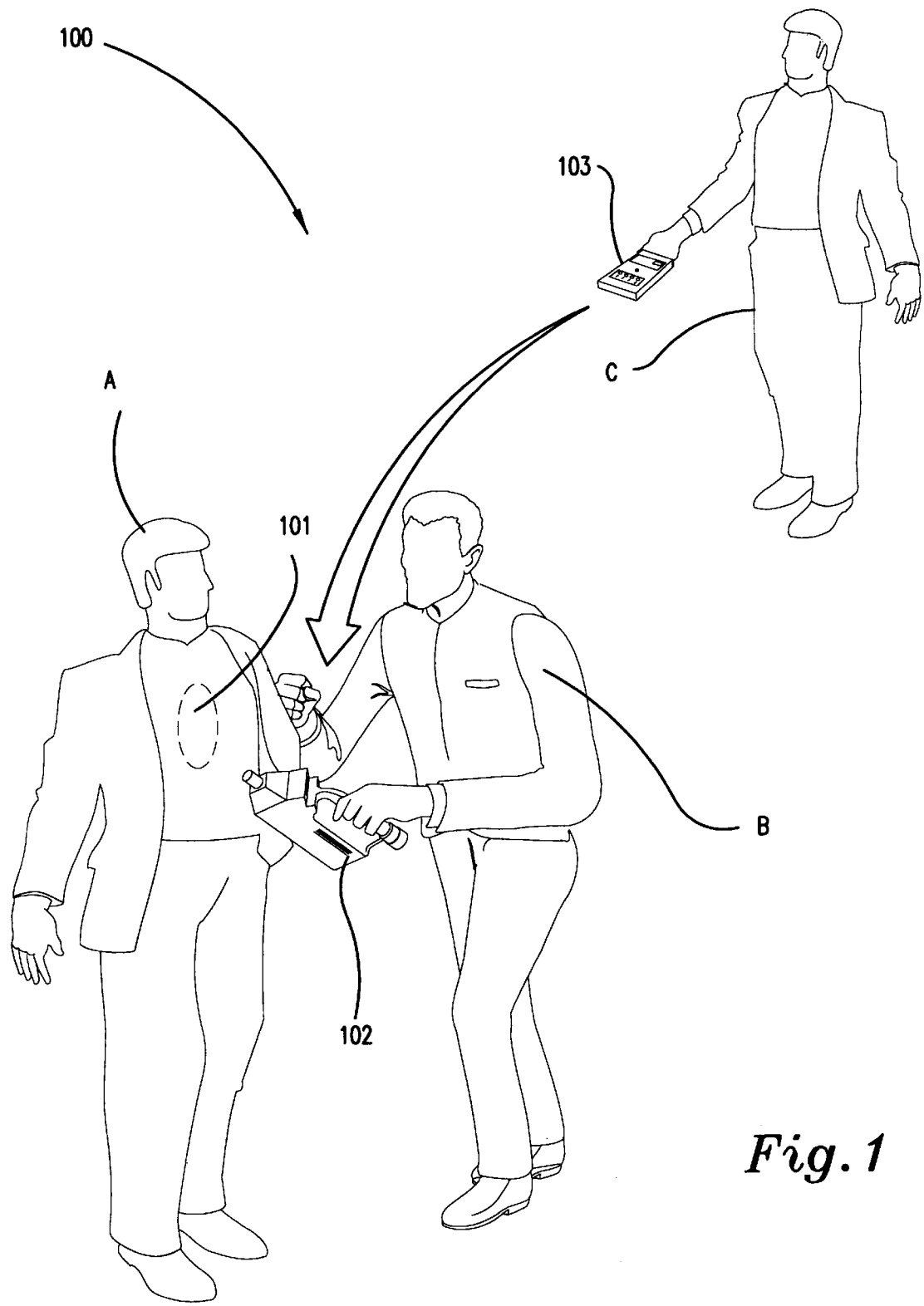
FIG. 1 is an environmental view showing a training situation using the PRID, hazardous material detector simulator, and instructor remote control of the present invention.

The present invention is primarily for use in a hazardous material training environment as shown in FIG. 1. During a training exercise 100, a number of PRIDs are placed in random hidden locations, shown here as 101 under the clothes of person A. A student B uses the simulated detector 102 to scan the object or person in question. An instructor C, observes the training exercise, and interjects any appropriate commands via remote control 103. It should be noted that the student B is unaware as to the location of PRID 101, and further, even in situations where the PRID is visible, the student B is unaware as to the programming of the PRID's or the detector's microcomputers. This is important in that the versatile nature of this system allows a programmed response to a PRID to range from full-scale meter deflection at close range, to no reading whatsoever, depending on the instructor's initial programming as well as any reprogramming done by remote 103. It should be noted that the term "meter deflection" refers to an analog meter, however, digital displays can also be used, (such as LCDs or LEDs).

Figure 2:
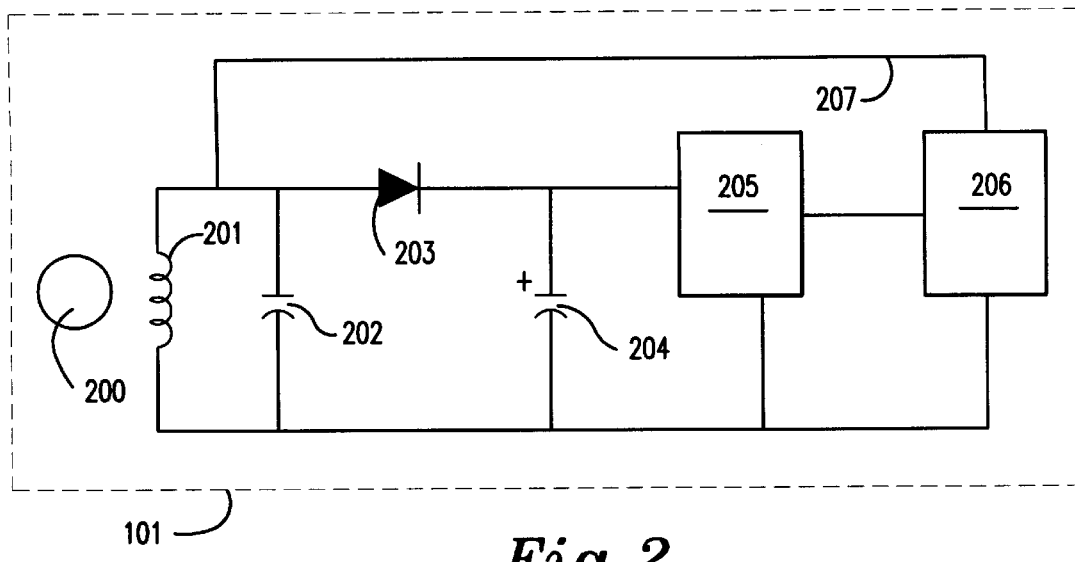
FIG. 2 is a block diagram of the PRID of the present invention.
Figure 4:
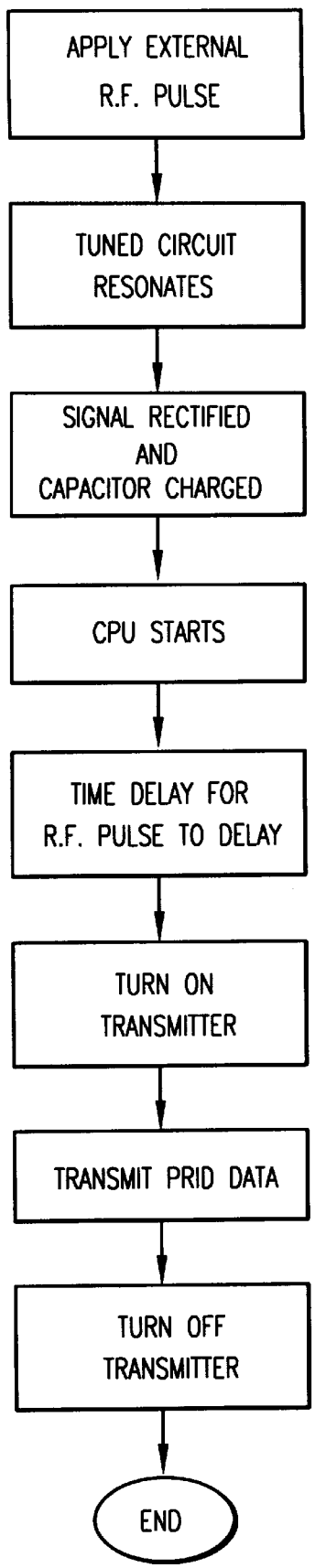
FIG. 4 is a flow chart showing operation of the PRID.

A block diagram of the passive radio identification device, PRID 101 of the present invention can be seen in FIG. 2. The operation of the PRID 101 is illustrated in the flow chart shown in FIG. 4. Inductor 201 and capacitor 202, make up a tuned circuit and their values are chosen so that the tuned circuit resonates at the radio frequency transmitted by the simulated detector 102. When the tuned circuit resonates, an AC voltage is developed across the tuned circuit. The AC voltage is rectified by diode 203, and the rectified voltage is used to charge capacitor 204. Once capacitor 204 is charged to a sufficient level, microcomputer 205 starts to operate. While in the preferred embodiment of the PRID the power is supplied by rectifying the RF energy pulse, the PRID can alternately be powered by an internal battery, and the RF pulse is used as a signal to the microcomputer 205 to power-up and initiate the following subroutine, thereby extending the usable life of the internal battery. Once the microcomputer 205 is supplied power or initiated, microcomputer 205 delays any action for a time period sufficient for the 50 ms pulse to decay. After the time period has passed, microcomputer 205 provides transmitter 206 with the PRID's identification code and a command to transmit. The transmitter 206 then uses frequency shift keying technology to modulate the RF signal, and transmits the RF identification signal onto line 207 and uses the tuned circuit as an antenna. After transmission, the transmitter is turned off, the charge on capacitor 204 decays, and the PRID is ready to receive any additional query pulse. Permanent magnet 200 is used to initiate the query pulse, or as the sole component to simulate the hazardous material source in further embodiments of the invention that are discussed in detail below.

Figure 3:
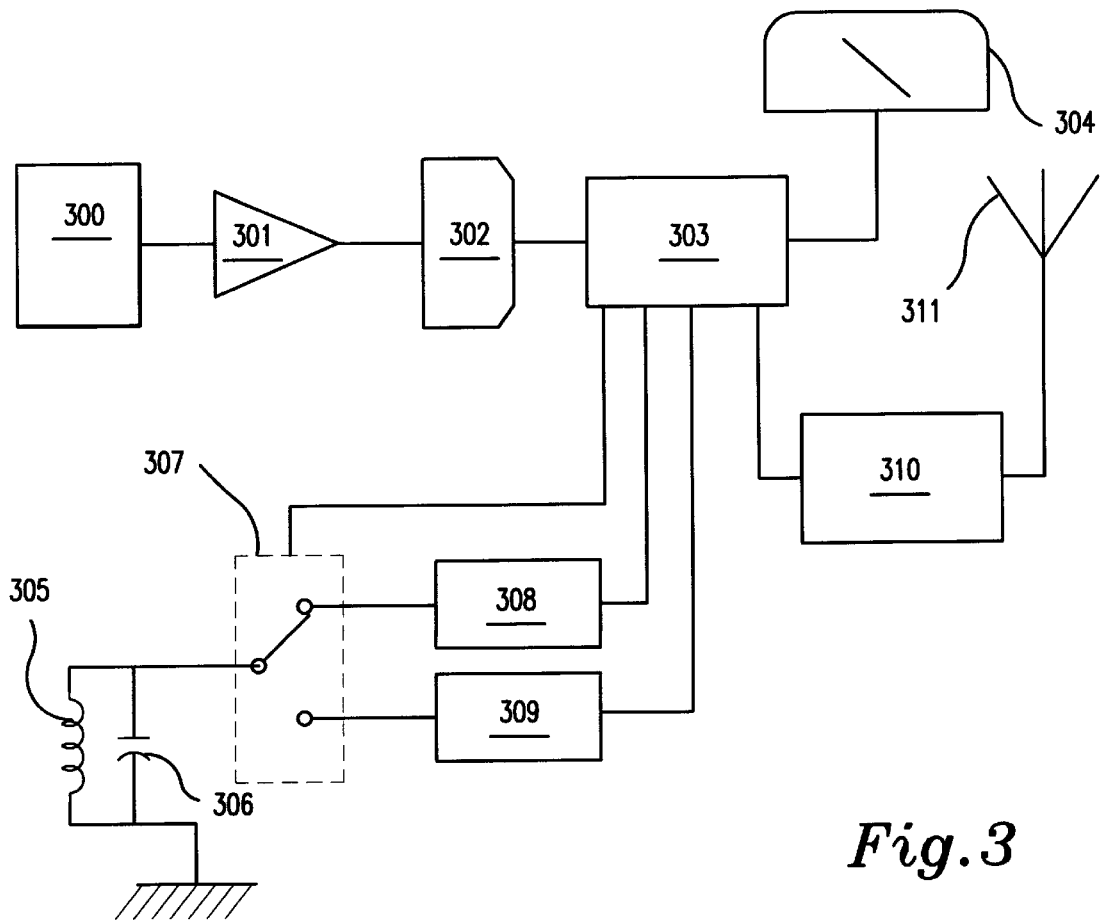
FIG. 3 is a block diagram of the hazardous material detector simulator.
Figure 5:
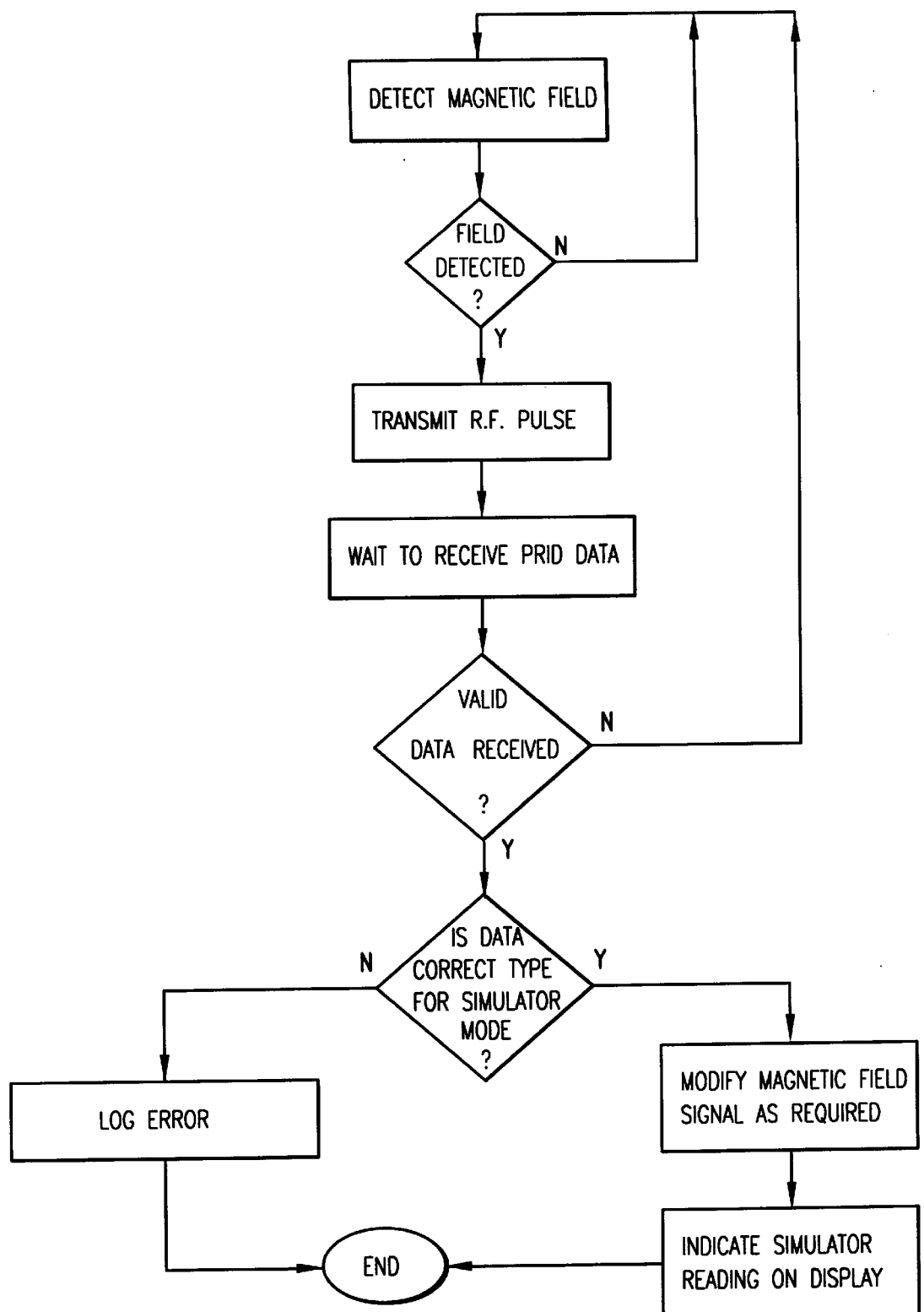
FIG. 5 is a flow chart showing operation of the hazardous material detector simulator.

A block diagram of the detector simulator 102 of the present invention can be seen in FIG. 3. The operation of the detector simulator 102 is illustrated in the flow chart shown in FIG. 5. It should be noted that FIGS. 3 and 5 show all necessary elements for operation of the system using the permanent magnet, and that embodiment will be discussed first.

When a student, (or other operator), places the simulated detector 102 in close proximity, (the magnet is preferably sized to make this distance 7–8"), to a PRID, Hall effect device 300 produces an output voltage proportional to the sensed magnetic field generated by permanent magnet 200. This output voltage is then amplified by amplifier 301 to a level usable by analog to digital, (A/D), converter 302. The A/D converter 302 then provides a digital signal to microcomputer 303 indicative of the presence and strength of the detected magnetic field. When the microcomputer first receives the signal indicative of a sensed magnetic field, the microcomputer 303 prompts transmitter 309 to transmit a 50 ms pulse of RF energy at the frequency that will cause the tuned circuit in the PRID to resonate. The transmitter is a carrier only system as only a burst of RF energy is needed to cause the tuned circuit in the PRID to resonate. At the same time, the microcomputer 303 energizes transmit/receive relay 307 to connect the transmitter to the simulated detector's tuned circuit, (comprised of inductor 305, and capacitor 306), that acts as an antenna. It should be noted that the transmit/receive relay 307 is given as one method of allowing a transmitter and receiver to share a single antenna, and several other known techniques can be employed to this end. In addition, the transmitter and receiver may be provided with separate antennas. After the 50 ms pulse has been transmitted, the microcomputer 303 deenergizes relay 307 to reconnect the antenna, (tuned circuit), to receiver 308. If no identification signal, or if an invalid identification signal is received, the microcomputer 303 restarts the process and again looks for a magnetic field detection signal. If, however, a valid identification signal is received, the microcomputer 303, determines if the simulated detector's mode, (selected by the student using selector switches on the simulated detector), is correct for the type of contamination the PRID is programmed to simulate, (via the identification signal). If an incorrect mode for the type of contamination the PRID is programmed to simulate, is selected, the output indication, (meter deflection or digital display), is modified, to simulate the output indication an actual hazardous material detector would provide in the same circumstances, and the microcomputer 303 logs the error into internal memory. The error information entered into internal memory includes: the level and type of contamination missed; the time the error was made, in terms of real time (when microcomputer 303 includes a real time clock), or in terms of elapsed exercise time (wherein T=0 at the start of the exercise); and the type of error made, (detector set to detect wrong material, confidence checker not used, etc.). In the event the correct mode is selected for the type of contamination simulated by the PRID, the microcomputer 303 determines the appropriate level of response, (meter deflection or numerical indication). It should be noted that the PRID can be queried on a regular basis, typically every 250 ms . Several factors are taken into consideration to determine the appropriate response. In embodiments where the magnet 200 is present, the identification signal contains information concerning the strength of the permanent magnet 200. The microcomputer 303 compares this information to the detected magnetic field strength information provided by the A/D converter 302, to determine the distance between the simulated detector 102 and the PRID 101. The identification signal also contains information concerning the level and type of the contamination. The microcomputer 303, compares the level and distance to determine the appropriate display. For example, α particle radiation requires that the detector be somewhat close, (approximately 1"), for an initial reading, while β particle radiation requires a distance of approximately 4–5" for an initial reading. Additionally, the change in the distance between the detector and the contamination influences meter readings differently for various substances. For example, when simulating α particle radiation the detector would need to be very close to the magnet to get any reading, but the reading would increase rapidly as the detector is moved closer. Another substance, however, may not need to be as close to get an initial reading, and would increase in a more linear fashion as the detector is moved closer. It should be noted that these are only given as examples, and the versatility of the present invention allows an unlimited range of types and levels of contamination to be simulated.

While the preferred embodiment of the present invention uses the permanent magnet 200, it is not a necessary component. In embodiments not using the magnet, the following changes in operation and construction are used. The simulated detector does not contain Hall effect device 300, amplifier 301 and A/D converter 302. Receiver 308 additionally contains an A/D converter to provide microcomputer 303 with digital information proportional to received RF energy. The detection of a magnetic field is not used to prompt transmission of the RF pulse. The microcomputer 303 periodically instructs the transmitter 309 to transmit the 50 ms pulse, (while also energizing transmit/receive relay 307 to attach the tuned circuit to the transmitter 309). If no valid identification signal is received, the microcomputer 303 continues to periodically transmit the 50 ms pulse. In the event a valid identification signal is received, the process continues as discussed above. The only other difference in operation when no magnet is used, is the calibration of the distance between the detector simulator and the PRID. While the magnetic embodiment uses magnetic field strength to determine this distance, the non-magnetic embodiment uses received RF signal strength. This is done by programming the PRID to transmit an identification signal that contains information concerning the strength of the RF signal transmitted by the PRID. The microcomputer 303 then compares this information with the received RF signal strength information provided by the receiver's A/D converter.

The major advantage in using magnet 200, is reduced consumption of power by the detector simulator. This is important as the detector simulator is a hand-held battery powered unit, and by periodically transmitting the RF pulse, (which requires approximately ½ ampere battery current), the batteries are drained rather quickly. It should be noted, however, that both the magnetic field strength as well as the received RF strength can be used in the same unit, (by simply providing an identification signal with information containing both magnetic field strength as well as transmitted RF energy, and providing the receiver with the A/D converter discussed above), to provide a more accurate and dependable method of calibrating the distance between the detector simulator and the PRID.

One of the most powerful training aids of the present invention is the use of the instructor's remote control device 103. The device itself, (which may be infrared or RF), is well known, (used by television sets, stereos, car alarms, etc.), and no further explanation of the physical device is deemed necessary. The signal transmitted by the device, preferably by radio telemetry link, includes commands to alter the detector simulator's responses to a specific PRID, a group of PRIDs, or all PRIDs. To receive the signal transmitted by the remote control device 103, the simulated detector is provided, for example, with a receiver 310 and an antenna 311 which are connected to the microcomputer 303 as indicated in FIG. 3. In the course of a training exercise, a student or group of students may be required to search and identify various sources of hazardous material contamination. After having located one or more of these sources, the students are then required to follow decontamination procedures appropriate for the type of contamination. These are the same procedures used in a true decontamination exercise, and the students do not remove or disturb the PRID in any way, as this would be unrealistic from a training point of view. The instructor observes the decontamination procedure to ensure it is correctly done. If the procedure would result in removal of the contamination source, the instructor, (by remote), can alter the programming of the microcomputer 303, to no longer respond to that particular PRID. If, however, the procedure would only remove part or none of the contamination, the instructor can alter the programming of the microcomputer 303, to provide a reduced indication on the display 304, (partial decontamination), or he can do nothing, which would maintain the initial display for that particular PRID. For complex exercise simulation, the instructor's remote 103 may also contain a hand held personal computer programmed to simulate various phases of a hazardous material detection exercise.

In a simulated chemical or nuclear attack, there are a number of parameters that can change over time. Again, the instructor's remote can be used to simulate these changes. For example, at the start of the exercise, a particular area may contain no contamination, but may become contaminated during the course of the exercise. This scenario is easily simulated using the instructor's remote 103. Initially, the simulated detector(s), (more than one may be in use), can be programmed to provide no response to a group of PRIDs, (those in the area in question). This can be done by additionally providing each PRID's identification code with a group identity. At a point in time when the instructor wishes to simulate a chemical, bacteriological or nuclear attack or accident, the instructor transmits a command to the simulated detector(s), to respond to the PRID(s), as if they were the type of contamination desired to simulate. Further, in the case of hazardous materials that tend to dissipate, or travel with the wind, the instructor can transmit a command to a single PRID or a group of PRIDs, to decrease the level of simulated contamination the simulated detector(s) display from one PRID or group of PRIDs, (due to dissipation or an upwind location relative to the simulated contamination), while increasing the level of simulated contamination the simulated detector(s) display from another PRID or group of PRIDs, (due to a downwind location relative to the simulated contamination). It should be noted that when a number of PRIDs is used, consideration must be given to the RF power transmitted by the PRIDs to avoid two or more PRIDs in close proximity causing mutual interference. The above comments apply equally to a system in which the simulated hazard is represented by radio and/or ultrasound.

In addition to the above features, the microcomputer 303 within each detector simulator, is capable of storing information as to the procedures used by the student operating that particular simulator. For example, many actual hazardous material detectors are used in conjunction with a confidence checker. A confidence checker contains a small amount of hazardous material, (or another material that affects the detector in the same way as the actual hazardous material), that is used to determine whether the detector is operating properly. A PRID can be used to simulate the confidence checker, and the microcomputer 303 can log, (into its internal memory), whether the PRID that is being used to simulate the confidence checker was first detected prior to the student using the detector to identify other simulated hazardous materials, (PRIDs, magnets, ultrasound), as well as ensuring that the confidence checker was used periodically, (perhaps every 30 minutes), to check proper functioning of the detector. In fact, the microcomputer 303 can record all of the detected signals regardless of whether these signals were displayed on the simulator. The recorded information can include the nature of the missed hazard, as well as the level and time duration of the missed hazard. This can be useful as a typical real-life scenario with chemical detection might be an operator trying to detect mustard agent when the hazard is actually nerve agent. Further, in some instances selecting a different detection mode, (type of hazardous material), without first checking that the initial mode results in zero or insignificant reading may constitute an error. At the end of the exercise, (or any suitable time), this stored information can be displayed on the simulated detector or downloaded using any of the well known techniques for computer information exchange, and the information can be used for further instruction. If desired, the errors encountered during a training exercise can be displayed as they occur, to allow a student to use the system as a self-training tool. When the errors are displayed in this manner, corrective action may also be auto-suggested via the display 304 or on a remote device such as a PC.

A further embodiment of the present invention uses ultrasound emitters to simulate the specific material. There are two methods the ultrasound emitters are used to simulate the specific material. The ultrasound emitters transmit an ultrasound signal at a specified frequency, and the simulated detector uses an ultrasound receiver to detect this signal. In the first method, this signal is a simple non-modulated frequency, that is used to simulate a specific material. When more than one material is to be simulated, the ultrasound emitters use more than one frequency. For example, a 25 kHz ultrasound signal may be used to simulate the presence of mustard agent, while a 33 kHz signal is used to simulate the presence of nerve agent. This embodiment has the advantage over the use of PRIDs, in that the ultrasound emitters can be placed as close to each other as desired without any mutual interference. This allows any size area to be simulated as being contaminated, simply by placing a number of the emitters in a desired pattern. The different frequencies can also be overlapped to simulate two different contaminates occupying the same space. This is possible because the simulated detector has separate receivers for the two frequencies, thus allowing simultaneous processing. In a further embodiment, the ultrasound emitters can be used in place of the PRIDs to provide the aforementioned identification signal. This is done by modulating, (using amplitude modulation, or pulsing the ultrasound signal, to thereby include the identification signal information encoded therein. The ultrasound receiver in the simulated detector includes a demodulator and an A/D converter to supply the information to the microcomputer inside the simulated detector. When the ultrasound emitters are used to transmit the identification signal, as with the RF PRIDs care must be taken to space the emitters far enough apart to avoid mutual interference.

In addition to the above embodiments, if only one type of contamination is simulated, the use of the PRID can be eliminated, and the magnet alone can act as the simulated source. When this is done, the instructor's remote can be used to modify the sensitivity of the probe to the magnetic field to achieve the above described results, A simulated hazardous material detecting exercise using the present invention will now be described. Initially, an instructor or group of instructors place a number of simulated material devices in appropriate areas. These areas would include: on the ground in a simulated contaminated area; on vehicles; on personnel; near barrels, (to simulate fuel vapors); on walls, (during training inside of structures); at a specified confidence checker location; and any other areas that the instructor(s) might wish to simulate the presence of certain materials. The material simulators would include: magnets alone; PRIDs with or without magnets; and ultrasound emitters. The simulated detector(s) can be configured to work with all of the material simulators with the following exceptions: the PRIDs used would need to be either with or without magnets to allow the simulated detector to either continuously, (every 250 ms ), query for identification signals or query when a magnet is detected; when PRIDs using magnets and magnets alone are both used, the simulated detector would need to be programmed to treat the magnets as magnets alone, (this operation is described above), when no identification signal is returned; and when using PRIDs or ultrasound emitters are used that transmit modulated signal containing the coded identification signal, these devices need to be placed far enough apart to avoid mutual interference, (as described above). Once the simulated material devices have been placed, a student or number of students are given simulated material detectors. Each of the simulated detectors has its own identity, and the instructor(s) are aware of which detector is which to allow separate reprogramming during the exercise. Each student is responsible for checking their detector prior to use, and an instructor observes this procedure. It should be noted that one or more of the simulated detectors can be placed in the self-help mode, thereby allowing some of the students to observe any errors made as they occur, as described above. If any errors are made while the students check the detectors, the instructor can reprogram the detector(s) to react accordingly, (for example, not removing a probe cover might result in reduced readings during the confidence check, and the instructor can reprogram the detector to reflect this lower reading). Once the equipment has been checked out, the students are instructed to search different areas for possible contamination. One of the students may be instructed to search an area including barrels of simulated fuel. An instructor prior to the exercise would have placed an ultrasound emitter close to the barrels to simulated leaking fuel or vapor, (the ultrasound emitter would be identifiable by the detector as a simulated fuel leak, either by the coded identification signal, or by pulsing the ultrasound signal when the ultrasound emitter is a carrier only type). The student would then be required to differentiate between the fuel leak and hazardous material contamination by the level of reading received, and the location of the signal, (near the barrels). Several areas of different contamination are normally simulated during an exercise. In addition, these areas can actually be changed during the exercise, by using the instructor's remote to reprogram the way the simulated detector(s) react to the simulated material devices. This can be done to simulate an attack during the exercise, to simulate dissipation of certain materials, to simulated wind-carried materials, or to simulated partial or complete decontamination. Some of the vehicles used in the exercise may be moved out of contaminated areas, and these vehicles would have simulated material devices that represent contamination that occurred while the vehicles were in the contaminated area. Some or all of the students participating in the exercise would also be fitted with simulated material devices, (usually under their clothing). These students would also be searched using the simulated detectors. At the end of the exercise, each detector is placed in a "readout" mode, (using a key switch on the bottom of the simulated detector), and an instructor would read the errors and procedure followed by the student using that particular detector during the exercise. The programming of the simulated detector can also include simulated equipment failure, and the way the student dealt with this failure can also be analyzed. For more complex operations, this information could downloaded into a personal computer, for complete analysis.

It is to be understood that the present invention is not limited to the embodiments described above, but encompasses any and all embodiments within the scope of the following claims.

I claim:

1. A system for simulating detection of hazardous materials comprising:
   a simulator for transmitting an identification signal simulating a hazardous material; and
   a detector having identification means for identifying said identification signal as a specific hazardous material, wherein said identification means includes a microcomputer programmed for identifying said identification signal as the specific hazardous material;
   wherein said detector includes means for activating said simulator when said detector is within communication range of said simulator, said means for activating the simulator includes a transmitter, said detector further includes a receiver for receiving said identification signal and means controlled by said microcomputer for switching between said transmitter and said receiver.

2. The system for simulating detection of hazardous materials according to claim 1, wherein said simulator includes a passive radio identification device, PRID, for transmitting said identification signal, and said means for activating activates said PRID.

3. The system for simulating detection of hazardous materials according to claim 2, wherein said simulator further includes means for generating a magnetic field, and said detector further includes means for detecting said magnetic field, whereby said detector activates said PRID when within communication range of said magnetic field.

4. A system for simulating detection of hazardous materials comprising:
   a simulator for transmitting an identification signal simulating a hazardous material, said simulator emits an ultrasound signal containing said identification signal and includes means for generating a magnetic field; and
   a detector having identification means for identifying said identification signal as a specific hazardous material, wherein said identification means includes a microcomputer programmed for identifying said identification signal as the specific hazardous material;
   wherein said detector includes means for activating said simulator when said detector is within communication range of said simulator and means for detecting said magnetic field, whereby said detector transmits an activation signal to said simulator when within communication range of said magnetic field, said detector further including a transmitter for activating said simulator, a receiver for receiving said identification signal, and means, controlled by said microcomputer, for switching between said transmitter and said receiver.

5. The system for simulating detection of hazardous materials according to claim 1, wherein said detector further includes means for monitoring a method of operating the detector and output means for displaying the operation of the detector to determine whether said method of operating the detector differs from a correct method of the operating the detector.

* * * * *